United States Patent
Bock et al.

(10) Patent No.: US 7,079,035 B2
(45) Date of Patent: Jul. 18, 2006

(54) METHOD AND APPARATUS FOR CONTROLLING AN ALARM WHILE MONITORING

(75) Inventors: Elizabeth A. Bock, Elm Grove, WI (US); George M. Hutchinson, Brookfield, WI (US); David A. Sitzman, Hubertus, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 371 days.

(21) Appl. No.: 10/440,626

(22) Filed: May 19, 2003

(65) Prior Publication Data

US 2004/0236187 A1    Nov. 25, 2004

(51) Int. Cl.
*G08B 23/00* (2006.01)
(52) U.S. Cl. .................... 340/573.1; 600/301
(58) Field of Classification Search ........... 340/573.1, 340/500, 501, 539, 5.8; 600/300, 301, 306, 600/323, 324, 346–348; 705/2, 3; 607/30–32, 607/60
See application file for complete search history.

(56) References Cited

U.S. PATENT DOCUMENTS

| | | | | |
|---|---|---|---|---|
| 5,464,012 A | * | 11/1995 | Falcone | 600/301 |
| 5,469,144 A | * | 11/1995 | Gradzki et al. | 340/603 |
| 5,865,736 A | | 2/1999 | Baker, Jr. et al. | 600/323 |
| 6,057,758 A | * | 5/2000 | Dempsey et al. | 340/539.12 |
| 6,315,719 B1 | * | 11/2001 | Rode et al. | 600/300 |
| 6,569,095 B1 | | 5/2003 | Eggers | 600/300 |
| 6,754,516 B1 | * | 6/2004 | Mannheimer | 600/323 |

OTHER PUBLICATIONS

Online Pattern Recognition in Intensive Care Medicine, Dr. R. Fried et al., 2001 AMIA Annual Symposium, Nov. 3-7, 2001 Washington, D.C., 7 pages.
Making ICU Alarms Meaningful: a comparison of traditional v. trend-based algorithms, R. Schoenberg M.D. et al., AMIA Annual Symposium, Nov. 6-10, 1999, Washington, D.C., 7 pages.
Diagnostic Monitoring in Anaesthesia Using Fuzzy Trend Templates for Matching Temporal Patterns, A. Lowe et al., Artificial Intelligence in Medicine 16 (1999) 19 pages.

* cited by examiner

*Primary Examiner*—Jeffery Hofsass
*Assistant Examiner*—Jennifer Mehmood
(74) *Attorney, Agent, or Firm*—Andrus, Sceales, Starke & Sawall (57) ABSTRACT

A method for monitoring a subject can include acquiring data from the subject, and dynamically adjusting an alarm limit based on the data. The method can also comprise determining a first value that is typical for the subject for the characteristic being monitored, determining a second value for the characteristic being monitored, and generating a comparison based on the two values. The method could also comprise setting a threshold for a characteristic being monitored, and decreasing the alarm limit if the data crosses the threshold. The method could also include setting an extremity limit. The following methods can be applied to the monitoring of a healthcare patient, or other subjects of interest. Also, the values used in the monitoring of the subject can be configured to be transferable from one monitor to another.

22 Claims, 5 Drawing Sheets

METHOD AND APPARATUS FOR CONTROLLING AN ALARM WHILE MONITORING

BACKGROUND OF THE INVENTION

Monitors are used to monitor all sorts of variables to look for the occurrence of certain noteworthy events. Many actions taken by a subject can generate events that generate data that looks like an alarm, but is merely an artifact. For instance, if a patient moves around, a sensor attached to the patient may generate a data signal that would be indicative of an abnormal condition. This false positive result (registering that an event has occurred when in fact no significant event has occurred) would preferably not result in an alarm being generated. It would be desirable to have a monitor that can indicate when an event has occurred where most of the indicated events are significant. It would also be desirable to avoid registering false positives, while avoiding false negatives (not registering the occurrence of a significant event).

Many subjects, such as patients, differ from each other in many respects that are material to monitoring. For instance, a typical person may have a normal systolic blood pressure of 120, whereas an individual's normal systolic blood pressure may be closer to 100. Some values of a systolic blood pressure may be reasonable for the typical person where they would not be as reasonable for the individual. A monitor that could use limits based on the characteristics of the subject, including typical values for the subject, would be preferable. A monitor that could use limits based on the historical characteristics of a subject would be desirable.

Additionally, readings from a patient may go from a high point in a range that is not alarming for a subject to a low point in the range that is also not alarming. While the values themselves may not be very alarming, the change in value may be significant. For instance, a value that is steadily dropping may be indicative of a problem that is gradually worsening. Also, a value that drops quickly may be a sign that something has gone wrong, even if the value remains in a normal range for the subject. A system that can indicate when the readings are fluctuating, when such fluctuation is important, would be preferable. A system that can identify a relevant event indicated by the fact that the readings are changing over longer periods of time would be desirable.

The teachings herein below extend to those embodiments which fall within the scope of the appended claims, regardless of whether they accomplish one or more of the above-mentioned needs.

SUMMARY OF THE INVENTION

One embodiment provides a method for sending an alarm based on monitoring of a patient. The method comprises determining a first value that represents a typical value for the patient for the characteristic being monitored, and processing the first value to set an criteria based on the first value.

Another embodiment provides a method for sending an alarm in a medical monitoring device. The method comprises setting a threshold for a characteristic being monitored, acquiring data from a patient for the characteristic being monitored, and setting an alarm criteria exceeding the threshold if the data crosses the threshold, the alarm criteria having a finite duration.

Another embodiment is directed to a method for sending an alarm in a medical monitoring device. The method comprises setting a threshold for a characteristic being monitored, acquiring data from a patient for the characteristic being monitored, and tightening an alarm criteria if the first data crosses the threshold.

Another embodiment provides a monitor for monitoring a characteristic of a subject. The monitor comprises a data acquisition device configured to input data from a subject of interest, and a processor. The processor is configured to determine a typical value for the characteristic being monitored, set alarm criteria based on the value, and send an alarm signal based on whether data acquired from a subject by the data acquisition device meets the alarm criteria.

Another embodiment is directed to a monitor for monitoring a characteristic of a subject. The monitor comprises a data acquisition device configured to acquire data from a subject, and a processor. The processor is configured to set a threshold value for a characteristic being monitored, set alarm criteria based on the threshold value if the data acquired from the subject by the data acquisition device crosses the threshold, the alarm criteria having a finite duration. The processor is also configured to send an alarm signal based on whether the data acquired from the subject meets the alarm criteria.

Another embodiment is directed to a method for sending an alarm using a medical monitor that is monitoring a patient. The method comprises acquiring first data from a patient, acquiring second data from a patient, generating a comparison based on the first data and the second data, and generating an alarm based on the comparison.

Another embodiment provides a method for use in monitoring a subject. The method comprises acquiring data to generate a profile for a characteristic of the subject that is being monitored where the profile changes over time, and dynamically adjusting alarm criteria based on the profile.

Another embodiment is directed to a method for monitoring a patient. The method comprises setting a threshold, acquiring data from the patient, and tightening alarm criteria based on when the acquired data crossed the threshold.

Other principle features and advantages of the invention will become apparent to those skilled in the art upon review of the following drawings, the detailed description, and the appended claims.

DETAILED DESCRIPTION OF THE PREFERRED EMBODIMENTS

In the following description, for purposes of explanation, numerous specific details are set forth in order to provide a thorough understanding of the present invention. It will be evident, however, to one skilled in the art that the exemplary embodiments may be practiced without these specific details. In other instances, well-known structures and devices are shown in block diagram form in order to facilitate description of the exemplary embodiments.

Figure 1:
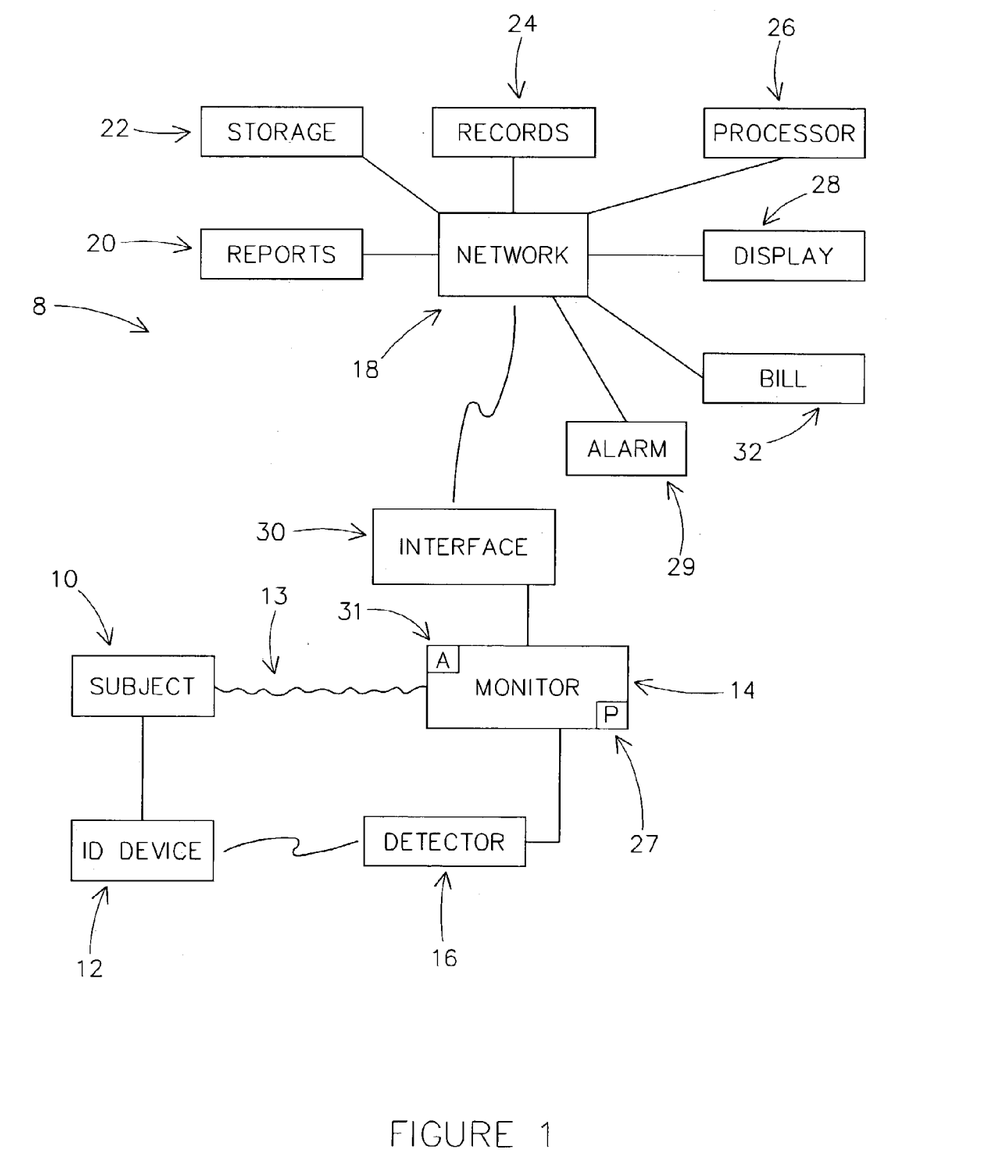
FIG. 1 is a diagram of a monitoring system according to one embodiment of the invention.

Referring first to FIG. 1, a monitoring system 8 comprises a monitor 14 and a network 18. Monitor 14 also comprises a network interface 30 that allows transfer of data to and from network 18. Network interface 30 is preferably configured to allow wireless transfer of data. More preferably, network interface 30 is configured to transmit data using a radio frequency. Network interface 30 may directly facilitate transfer of data across a network for the monitor, or may facilitate transfer of data by coupling the monitor to some other device that can directly facilitate transfer.

The data transferred from monitor 14 to network 18 can be raw data or can include data that has been processed. Also, data can be transferred to monitor 14 to aid, configure, and/or operate a function of monitor 14, or can serve some other purpose relating to monitor 14. For instance, the data may include a subject's history or can include previous values used when monitoring the particular subject.

Network 18 can be any type of network across which data can be transferred. For example, network 18 can be a local area network, a wide area network, and/or the Internet. Network 18 is coupled to a report generator 20, a data storage device 22, a record keeping device 24, a processor 26, and a display 28. Report generator 20 can generate a report based on, data storage device 22 can store, record keeping device 24 can make or add to a record based on, processor 26 can process, and display 28 can display data acquired by a data acquisition device 13 of monitor 14.

Monitor 14 also includes processor 27. Processor 27 may be any signal processing circuitry, such as one or more microprocessors in combination with program logic stored in memory. Processor 27 may be made of a series of sub-processors where each sub-processor performs one of the functions of processor 27. Further, processor 26 may perform the functions of processor 27. Further still, processor 27 and processor 26 may be sub-processors of another processor that is responsible for the various functions.

Figure 2:
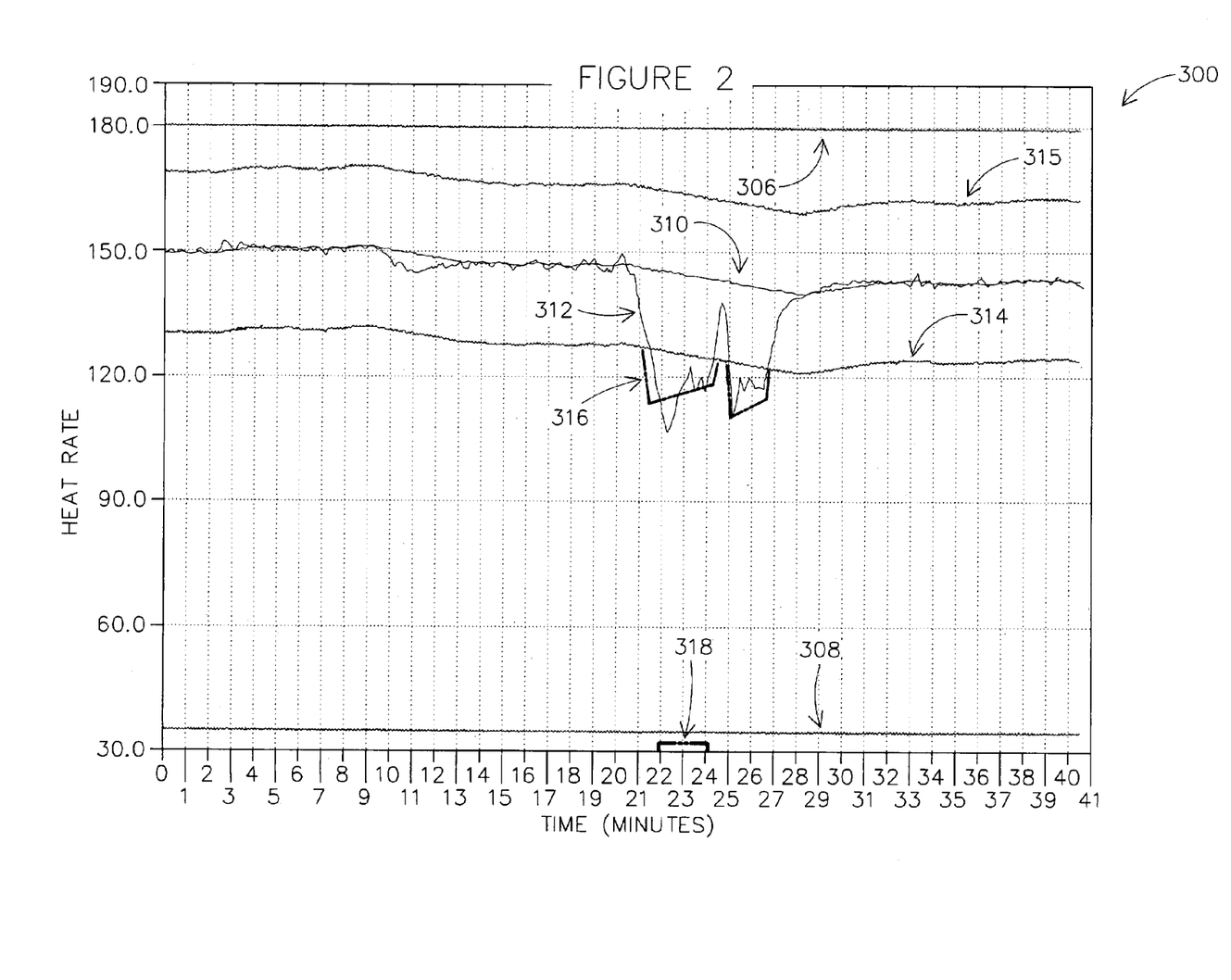
FIG. 2 is an illustration of alarm limits as alarm criteria where the limits are dynamically adjusted according to one exemplary embodiment of the invention.

Referring next to FIG. 2, a plot of data obtained from a monitor according to one embodiment can be seen in graph 300. Graph 300 shows a plot of heart rate (y-axis) over time (x-axis) according to one exemplary embodiment of the invention. Graph 300 shows an upper extremity limit 306, a lower extremity limit 308, a calculated representative value 310, and acquired data stream 312. Graph 300 further includes tracking thresholds 314 and 315, alarm limit 316, and alarm indicator 318.

Monitor 14 generates an alarm if the instantaneous heart rate falls outside extremity limit 306 or 308. Extremity limits 306 and 308 represent values that are extreme for the characteristic being monitored. For instance, if a patient is being monitored, the value may represent a value for the characteristic that is unlikely to be acquired from a patient who does not require immediate attention, or a value for the characteristic that represents that the patient is having (or soon will have) complications.

Monitor 14 also generates an alarm if the heart rate deviates in a predetermined manner from a calculated representative value 310. To this end, calculated representative value 310 is increased incrementally if acquired data stream 312 is greater than calculated representative value 310 at a point in time 304. This can be seen between the twenty-ninth minute and the thirty-second minute. Calculated representative value 310 is decreased incrementally (decremented) if acquired data stream 312 is less than calculated representative value 310 at a point in time 304. This can be seen between the twenty-first minute and the twenty-eighth minute.

Tracking threshold 314 is set based on calculated representative value 310. Tracking threshold 314 can be set based on a percentage difference from calculated representative value 310, based on a set amount away from calculated representative value 310, and/or based on the standard deviation of the trend (for example, as the standard deviation of calculated representative value 310 increase, the gap between calculated representative value 310 and tracking threshold 314 is increased). Tracking threshold 314 can also be set based on a combination of the previously mentioned factors, and/or any number of other factors.

Alarm limit 316 is set when acquired data 312 crosses tracking threshold 314. Alarm limit 316 can likewise be set based on any number of factors. Alarm limit 316 can be based on calculated representative value 310, tracking threshold 314, and/or any other value (of course basing alarm limit 316 on tracking threshold 314 also means that alarm limit 316 is based on calculated representative value 310 if tracking threshold 314 is based on calculated representative value 310). Alarm limit 316 is pre-configured to decrease over time as can be seen between minutes 21.5 and 24.5.

Once alarm limit 316 is set, if acquired data 312 crosses alarm limit 316 an alarm is generated as represented by bar 318. Examples of acquired data exceeding alarm limit 316 can be seen between minutes 22 and 22.8, again at about minute 23.3, and again at about minute 24. The alarm persists until alarm limit 316 is removed. The alarm can also be configured to persist based on various other criteria. For instance, the alarm may persist until acquired data no longer exceeds tracking threshold 314 or some other threshold, the alarm may be configured with a hysteresis to persist for a certain duration after acquired data 312 crosses alarm limit 316, and/or the alarm may be configured to persist until a user resets or acknowledges the alarm (i.e. it can be latching). The duration of the alarm may alternatively be based on many other factors.

In this exemplary embodiment, the value for alarm limit 316 at a point in time can be defined by the equation AlarmCurve(t)=K+sp$\sqrt{t}$, where K is the value of alarm limit 316 when alarm limit 316 is set and "sp" is the rate at which the curve declines (the rate of decay 434). The value of K can be based on calculated representative value 310, acquired data 312, or some other value. The values used to calculate K and sp can be different at different points in time, and can be different for a lower alarm limit and an upper alarm limit.

Figure 3:
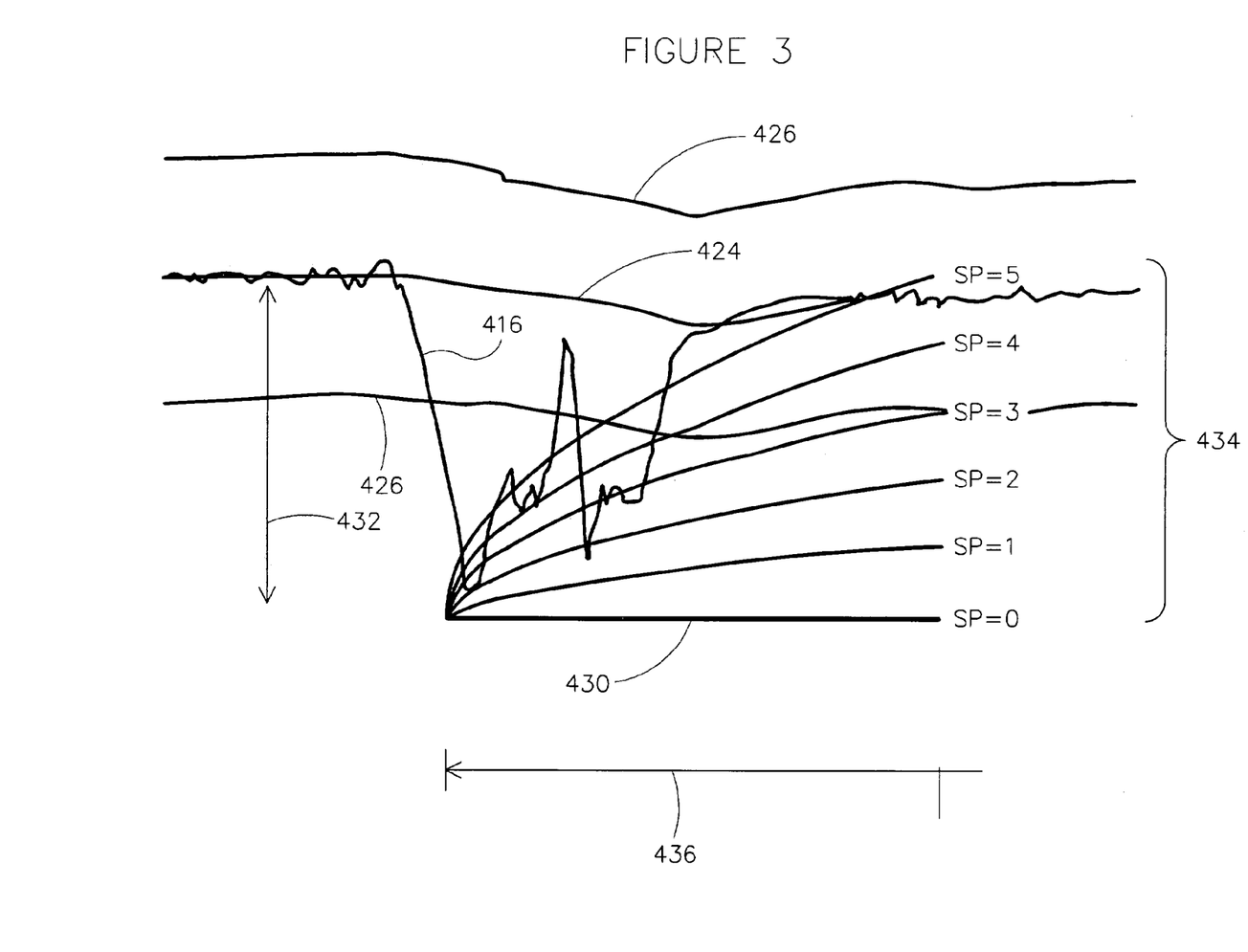
FIG. 3 is an exemplary illustration of an alarm limit that is set and that tightens when the acquired data crosses the tracking threshold according to one aspect of the invention.

Referring to FIG. 3, alarm curve 430 is calculated based on an excursion value 432 representing the maximum excursion from calculated representative value 424. Excursion value 432 can therefore be set such that if acquired data stream 416 exceeds calculated representative value 424 by more than excursion value 432, alarm curve 430 will be crossed. Alarm curve 430, however, can further include a decay rate 434, or speed of curve. Decay rate 434 represents the rate at which alarm curve 430 approaches calculated representative value 432 from excursion value 432. Alarm curve 430 may be represented by the equation: AlarmCurve(t)=K±sp$\sqrt{t}$ where K is calculated representative value 310±excursion value 432, sp is rate of decay 434, and t is time. Although a single alarm curve 430 has been described, a variety of curves and alarm thresholds 428 can be used. Alarm threshold parameters 438, such as the illustrated excursion threshold 432, decay rate 434, and reset time 436 may be adjusted by a user to adjust alarm thresholds 428.

Figure 4:
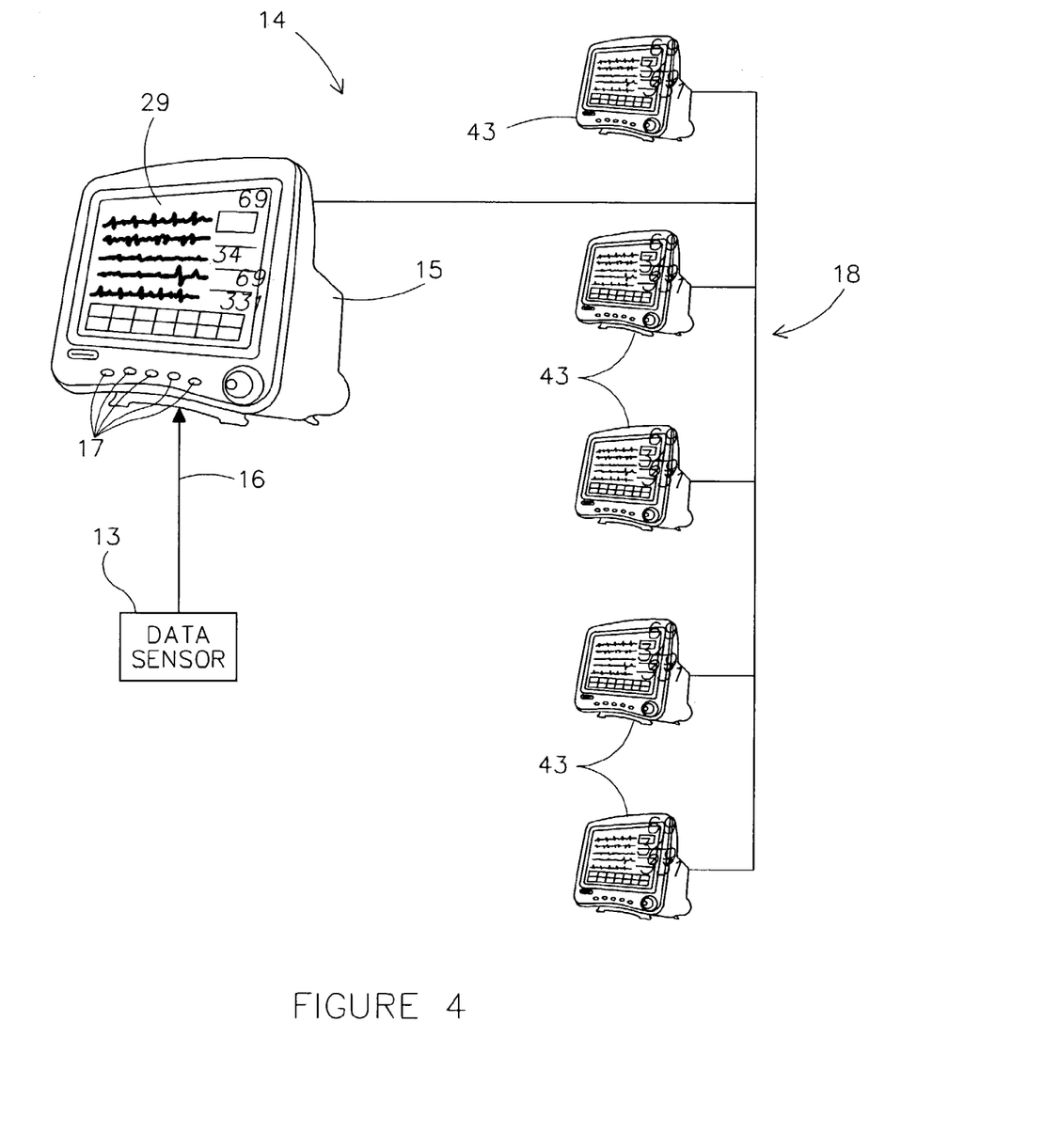
FIG. 4 is another exemplary embodiment of a monitoring system according to one aspect of the invention where a plurality of monitors are networked together.

Referring now to FIG. 4, a monitor 14 includes a controller 15 in communication with a data acquisition sensor 13 in order to receive a real-time data stream. The controller 15 may be utilized in combination with a variety of interactive elements such as a display 29 and control features 17 as would be comprehended by one skilled in the art. In one contemplated embodiment, the data acquired by data acquisition sensor 13 is physiological data from a patient. These characteristics include, but are not limited to, heart rate, arterial blood pressure, SpO2, CO2, EtC2, respiratory rate, and a variety of other patient physiologic responses. Also, a host of amplifiers, filters, and digitization elements may be utilized in combination with data acquisition sensor 13 as would be understood by one skilled in the art.

The extremity limits 306 and 308, tracking thresholds 314 and 315, calculated representative value 310, and incoming acquired data stream 312 can all be displayed on the display 29 such that a user can quickly and easily asses the status and settings of a subject 10. In addition, it is contemplated that the rate at which the calculated representative value is adjusted, the tracking threshold parameters, and the alarm parameters may also be displayed. Alteration of these parameters utilizing the control features 17 allows a user to fine tune the present system for a particular subject. By displaying changes in the settings, a user can be provided with a more adjustable system for generating alarms. Control features 17 could comprise a single knob that sets a single tolerance factor. The tolerance factor could then be used to adjust the various values used while monitoring. The single knob may have settings that represent tolerances from loose (alarms would generally appear less commonly) to tight (any deviation may be important).

Monitor 14 could also be networked to monitor assemblies 42 such that a subject can be moved from a single monitor 14 to any of the networked assemblies 43 while retaining information regarding calculated representative value 310, the tracking and alarm threshold calculations/parameters, and the update speed. This could allow users the ability to move a subject throughout the network while retaining all the vital monitoring information specifically set to the subject. Additionally, this could prevent monitoring from needing to start over from scratch after a move. It is contemplated that the subject can be identified after a move to a new monitor in a variety of fashions. Users may enter a subject id number into a networked monitor 43. Alternatively, the subject may be selected from a list or database retained on the network. In other embodiments, the information may be saved onto a portable memory device for transfer to the new monitor.

Figure 5:
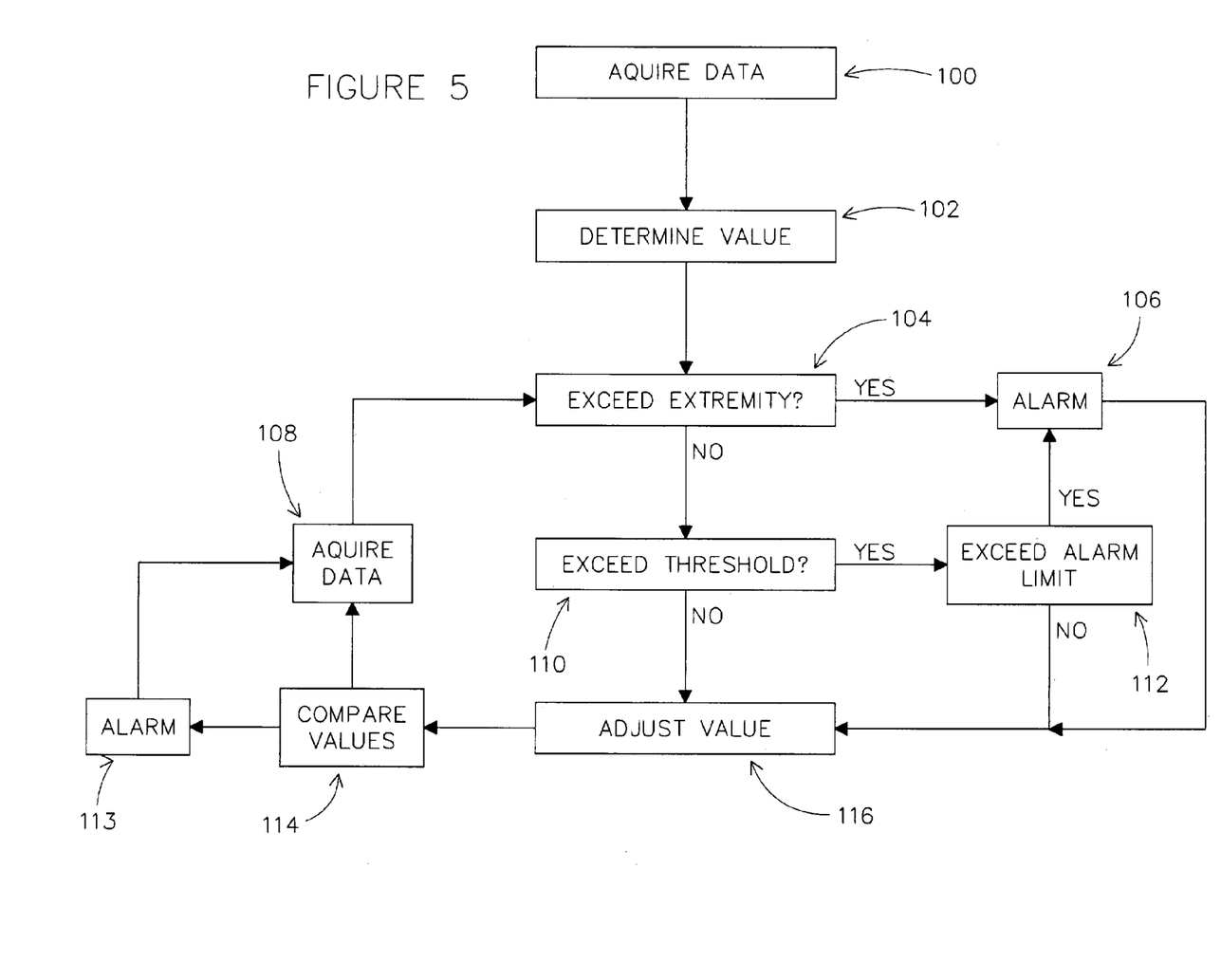
FIG. 5 shows an exemplary flow diagram for monitoring a subject according to one aspect of the invention.

Referring now to FIG. 5, data is acquired from a subject at block 100. The data could additionally be acquired from a database on a storage device 22, which storage device 22 could be connected to a monitor 14 over a network 18. Once data is acquired, a representative value is calculated at block 102. The value can be based on data acquired from a subject, can be data manually inputted, can be based on a tolerance factor, etc. The value can be equal to a data value or it can be some function of the data value. For instance, when monitoring blood oxygenation levels, the value can be equal to the current or typical level of oxygen in the monitored patient's blood, can be a function of both the current or typical level of oxygen in the monitored patient's blood and a standard blood oxygenation level for a typical person, can be based on a function that considers historical levels of blood oxygenation of a particular patient, etc. The representative value calculated at block 100 typically represents a normal value (or some function of a normal value) for the subject for the characteristic being monitored. For a patient, the representative value calculated at block 100 may also take into consideration the medications being taken and/or the treatments being administered.

Once the representative value is calculated at block 102, a determination is made based on whether the value crosses an extremity limit 104. If it does, an alarm is sent at block 106. The extremity limit represents a value that is extreme for the characteristic being monitored. The limit may be extreme in general, or may be extreme given the subject's characteristics and other values. An extremity limit is most useful if the tracking threshold or the alarm limit are ever allowed to cross the extremity limit. The extremity limit could alternatively be incorporated into a function used to determine a value of a tracking threshold or an alarm limit (i.e. the maximum/minimum the value of the alarm limit can be is the extremity limit value).

If the data does not cross the extremity limit at block 104, a determination is made at block 110 as to whether the data crosses a tracking threshold (such as 314 and 315) at block 110. The tracking threshold can be a preset amount different than the calculated representative value, can be some function of the calculated representative value, or can be based on some other typical value of the subject. An example of a function of the calculated representative value may include setting the tracking threshold based on how different the calculated representative value is from a typical value for an average subject, i.e., if the subject is a person, if a typical heart rate range is set between 60 and 80 beats per minute and the determined value for heart rate is 100 beats per minute, the exemplary function may set the high limit at 150 beats per minute whereas if the determined heart rate is 54 beats per minute, the exemplary function may set the high limit at 130 beats per minute. The tracking threshold may also be set based on the variability of the acquired data (i.e. if the standard deviation of the acquired data is large, then the tracking threshold is set farther from the calculated representative value 310, and if the standard deviation is small, then the tracking threshold is set closer to the calculated representative value 310).

If the data does cross the tracking threshold at block 110, a determination is made at block 112 as to whether the data meets an alarm criteria at block 112. The alarm criteria of block 112 is preferably affected by the fact that the data crossed the tracking threshold at block 110. Ways that the determination of block 110 may affect the alarm criteria of block 112 include setting the alarm criteria based on the determination of block 110, and/or tightening the alarm criteria of block 112 based on the determination at block 112. For example, the alarm criteria at block 112 may continually exist, but will tighten if the data crosses the threshold at block 110.

If the alarm criteria of block 112 is set to tighten if the tracking threshold is crossed, the duration of tightening can be preset, can be based on a tolerance factor, can be based on the results of other monitors, can be based on whether prior acquired data did and/or how close prior acquired data was to meeting the alarm criteria, can be based on a subject's history, can be based on the trend of the acquired values, can be based on whether the data continues to exceed the tracking threshold, and/or can be based on some other factor.

Sending an alarm at block 106 could involve a variety of factors. Also, some users may desire to include additional steps when sending an alarm at block 106. Some additional steps may include checking for the signaling of other alarms based on other criteria, other settings relating to the monitor or the monitored subject, customized settings for a particular facility/user, etc.

If an alarm is sent at block 106, the data does not meet the alarm criteria at block 112, or the data does not cross the tracking threshold at block 110, the calculated representative value is adjusted at block 116. The adjustment can be made every time, every set period of time, a time period based on the difference between the data and the calculated representative value, etc. The rate of adjustment can also be based on the amount of data acquired since the last adjustment, and/or the amount of agreement of the data (such as standard deviation) since the last adjustment. Also, when an acquired data value results in an alarm at block 106 (or meets some other criteria), block 116 may be skipped. Skipping block 116 may be one way of avoiding the incorporation of data that is not representative of a typical value for the subject for the characteristic being monitored.

Adjustment to the tracking threshold and/or the calculated representative value can be made in any number of ways based on the acquired data. For instance, if the newly acquired data point is greater than the calculated representative value, then the calculated representative value may be increased by a preset amount. This process could also be the reverse if the newly acquired data point is less than the calculated representative value.

Also, various data can be used to adjust the value at block 116. For instance, every value may be used unless the value results in an alarm at block 106, crosses the threshold at block 110, or meets some other criteria for non-inclusion. Also, the most recent data may be more heavily weighted, older data may be ignored, and/or some other criteria may be used.

Instead of adjusting the calculated representative value at block 106, the value of the tracking thresholds and/or alarm criteria can be adjusted directly. For instance, a tracking threshold may be reset based on whether the average value of the newly acquired data is greater than or less than a median point between two tracking thresholds (or than a point a certain distance from the threshold)—raising the threshold if greater, and lowering the threshold if less. The criteria for adjusting these values can also include factors such as those mentioned previously for adjusting the typical value.

Once the typical value is adjusted at block 116, values can be compared at block 114. Comparison at block 114 can include a determination whether a comparison of recorded values should be made. The determination may be based on time, on number of recorded values, or on some other criteria. If the determination is made based on time, the amount of time between values in the comparison is preferably greater than about 10 minutes, and more preferably, the values are separated by at least about 30 minutes. The amount of time between values is also preferably no more than about twenty-four hours, and more preferably no more than about 4 hours.

If based on amount of data received, the limits for amount of data would preferably be chosen such that they would generally meet similar time frames.

If a comparison is to be made at block 114, the comparison may be based upon two or more values, or two or more sets of values. Further, the comparison may include determining the difference in values, the comparison could include a trend analysis, and/or the comparison could include any number of other criteria. The comparison can be based on a plurality of the past values equally, a time weighted comparison of the values, a trend analysis of the values, a comparison of a small number of values, etc.

The comparison at block 114 could also include determining the change in a patient's values over time (i.e. determine the slope of the values). If slopes are determined, a plurality of values can be used to generate a plurality of slopes. For instance, each slope can represent an average change over a two or three minute time period. The values of a plurality of slopes can be compared. This comparison can include calculating a mean value and a standard deviation of the slopes over a set period, such as two or three hours or two or three days. A comparison of the slopes may be used to give an idea of the condition of a patient (for instance a patient who is steadily getting worse). For instance, a patient with a mean slope that shows decreasing values with respect to time and a low standard of deviation may be gradually worsening. This may be judged by comparing the mean slope and/or standard deviation to preset thresholds.

An alarm can be then sent at block 113 based on the comparison of block 114. The alarm can be based on whether the results of the comparison exceed a preset limit, based on a tolerance factor, based on other characteristics of the subject, and/or based on some other criteria.

Once the values have been compared at block 114, data can be acquired at block 108, and the process can proceed back to block 104.

A tolerance factor can be used to affect the parameters that are used. For example, a tolerance factor can be used to set the typical value, a tracking threshold, an alarm criteria, the rate at which values are adjusted, the rate at which an alarm criteria tightens, etc. A tolerance factor can also be used to affect the sensitivity allowed for the comparison at block 114.

The tolerance factor can be based on a number of different things. For example, the tolerance factor can be based on a factor chosen by a user, a subject's history, a subject's reason for being monitored, other measured values of a patient, the value of the typical value calculated at block 102 or adjusted at block 116, and/or some other criteria. Additionally, the tolerance factor may be adjusted by a user, may be adjusted based on information relating to subject 10, and/or may be adjusted based on the amount of data inputted from subject 10 (the more data that has been inputted, the more likely the alarm criteria accurately represents the subject). The tolerance factor may change over time and may be different for different applications of the alarm criteria to the subject 10.

Referring again to FIG. 1, monitor 14 comprises an identity detector device 16 configured to identify a subject 10. Identity detector device 16 can identify subject 10 by detecting an identification device 12 associated with a subject of interest 10. Identification device 12 can be a card or other object associated with the subject. Identification device could be used-for wireless identification of subject 10 and/or identification device 12 could be a computer readable medium.

Also, bill generator 32 can generate a bill based on the use of monitor 14. Bill generator 32 can generate a bill for the use of monitor 14, or can integrate the use of monitor 14 into a larger bill to be sent. Bill generator 32 can also monitor the usage of monitor 14, and generate reports based on usage of monitor 14. Bill generator 32 can also be used to send a notice to a person across network 18 indicating that monitor 14 is being used and billed. People that may desire receiving such a notice might include a patient's primary physician, a treating physician, an insurance carrier, and a patient. Delivering a notice to an insurance carrier may allow faster approval for sudden, unexpected usage of monitor 14. This would allow a hospital to collect funds sooner, and would allow a patient to worry less about obtaining coverage after treatment has been completed. Once the bill is generated, it can then be sent physically or electronically to a recipient. The recipient may be a computer at an insurance company that calculates the extent of coverage and the amount to be paid based on the usage of monitor 14.

Further, an alarm signal sent by processor 27 may be sent to an alarm signaling device 31 physically connected to processor 27, or may be sent to an alarm signaling device 29 located remote from processor 26. Remote alarm signaling device 29 may be a part of a pager or some other type of communication device. Remote alarm signaling device 29 could also be located at a discrete location such as at a nurse's station in a health care facility.

Alarms generated by alarm signaling devices 29 and 31 may take on any form including, but not limited to, an audible sound, a visual indicator, a message, and a vibrating alert. The alarm generated by alarm signaling devices 29 and 31 can further include a message indicating the reason for the alarm. The alarm could also be differentiated based on a number of criteria including the type and severity of the event causing the alarm. Further, if a system has more than one alarm signaling device, the device that signals the alarm could be differentiated based on a number of criteria including the type and severity of the event underlying the alarm.

Reference to "tightening" of alarm criteria means that more situations will be covered by the alarm criteria. For instance, when the alarm criteria includes an alarm limit whose value is set based on the value of a typical value for a subject, tightening the alarm criteria could include reducing the difference between the alarm limit and the typical value.

Reference to "dynamically tightening" the alarm criteria refers to a situation, as in FIG. 3, where the alarm criteria continues to tighten over a set period of time.

The invention has been described with reference to various specific and illustrative embodiments and techniques. However, it should be understood that many variations and modifications may be made while remaining within the spirit and scope of the invention. Also, while the invention is particularly useful for patient monitoring, the invention is applicable to other monitoring activities as well.

What is claimed is:

1. A method for monitoring of a patient, comprising:
   acquiring data from the patient;
   setting a threshold; and
   dynamically adjusting an alarm criteria based on the data at the time the data exceeds the threshold wherein the alarm criteria includes an alarm limit, and the alarm limit is dynamically adjusted based on the data, and further wherein the alarm limit is pre-configured to decrease over time.

2. The method of claim 1, further comprising generating an alarm based on whether the data meets the alarm criteria.

3. The method of claim 1, further comprising determining a value that is typical for the patient for the characteristic being monitored.

4. The method of claim 3, wherein determining the typical value comprises calculating the typical value based on a plurality of acquired data points.

5. The method of claim 1, wherein:
   the alarm criteria comprises
   an alarm limit whose value is set based on a value that is typical for a characteristic being monitored; and
   an alarm limit that represents a value that is extreme for the characteristic being monitored; and
   the alarm limit based on the typical value is dynamically adjusted based on the data.

6. The method of claim 5, further comprising sending an alarm if the data crosses the extreme alarm limit or if the data crosses the alarm limit based on the typical value.

7. The method of claim 1, further comprising determining a value that represents a typical value for the patient for the characteristic being monitored, wherein the threshold is set based on the typical value.

8. The method of claim 1, further comprising determining the alarm criteria based on a tolerance factor.

9. A monitoring system for monitoring a characteristic of a subject, comprising:
   a data acquisition device configured to acquire data from a subject of interest; and
   a processor configured to dynamically adjust an alarm criteria based on the data acquired from the subject, wherein the processor adjusts the alarm criteria at the time the data exceeds a threshold wherein the processor dynamically adjusts the alarm criteria by dynamically adjusting an alarm limit wherein the alarm limit is pre-configured to decrease over time.

10. The monitoring system of claim 9, further comprising an alarm sending device configured to send an alarm based on whether the data acquired from the patient meets the alarm criteria.

11. The monitoring system of claim 9, wherein the processor is configured to set an extremity limit.

12. A method of patient physiologic monitoring comprising:
    receiving a real-time physiologic data stream from a patient;
    calculating a representative value using the real-time physiologic data stream;
    calculating at least one threshold based on the representative value;
    monitoring the real-time physiologic data stream to determine if it has crossed the at least one threshold; and
    calculating an alarm limit when the real-time physiologic data stream crosses the at least one threshold, the alarm limit based on the representative value wherein the alarm limit is pre-configured to decrease over time.

13. The method of claim 12, further comprising generating an alarm when the physiologic data stream crosses the alarm threshold.

14. A method as described in claim 12, wherein calculating a representative value comprises incrementing the representative value when the real-time physiologic data stream rises above the representative value.

15. A method as described in claim 12, wherein calculating a representative value comprises decrementing the representative value when the real-time physiologic data stream drops below the representative value.

16. A method as described in claim 12, wherein calculating at least one threshold comprises calculating the at least one threshold as a percentage of the representative value.

17. A method as described in claim 12, further comprising:
    continuously comparing the real-time physiologic data stream to at least one extremity limit; and
    generating an alarm if the physiologic data stream crosses the at least one extremity limit.

18. A method as described in claim 12, further comprising networking the representative value such that when a patient is moved to any of a plurality of networked monitors, the monitors use the same representative value.

19. The method of claim 12, wherein calculating the alarm limit comprises calculating the alarm limit based on an excursion value and a decay rate.

20. A method for monitoring of a patient, comprising:
acquiring data from the patient; and
dynamically adjusting a threshold based on the data;
setting an alarm limit; and
generating an alarm based on whether the data crosses the alarm limit wherein the alarm limit is pre-configured to decrease over time.

21. The method of claim 20, wherein a value of the alarm limit is set based on a value of the tracking threshold.

22. The method of claim 20, further comprising determining a value that is typical for the patient for the characteristic being monitored.

* * * * *